United States Patent [19]

Wiktor

[11] Patent Number: 4,969,458
[45] Date of Patent: Nov. 13, 1990

[54] INTRACORONARY STENT AND METHOD OF SIMULTANEOUS ANGIOPLASTY AND STENT IMPLANT

[75] Inventor: Dominik M. Wiktor, Cranford, N.J.

[73] Assignee: Medtronic, Inc., Minneapolis, Minn.

[21] Appl. No.: 69,636

[22] Filed: Jul. 6, 1987

[51] Int. Cl.⁵ ............................................. A61M 29/02
[52] U.S. Cl. ...................................... 606/194; 623/13; 606/108
[58] Field of Search .................... 128/334 R, 341–344; 623/13

[56] References Cited

U.S. PATENT DOCUMENTS

| | | | |
|---|---|---|---|
| 3,842,441 | 10/1974 | Kaiser | 128/334 R X |
| 4,553,545 | 11/1985 | Maass et al. | 128/341 |
| 4,560,374 | 12/1985 | Hammerslag | 128/344 X |
| 4,649,922 | 3/1987 | Wiktor | 128/344 |
| 4,665,918 | 5/1987 | Garza et al. | 128/343 |
| 4,800,882 | 1/1989 | Gianturco | 128/343 |

FOREIGN PATENT DOCUMENTS 1205743  9/1970  United Kingdom ................ 128/343

Primary Examiner—Dalton L. Truluck
Attorney, Agent, or Firm—Robert J. Klepinski; Joseph F. Breimayer

[57] ABSTRACT

A device to be used as a vascular stent comprising a cylindrical open-ended wire component made of a low memory metal such as copper alloy, titanium, or gold, providing a radial support from within a blood vessel after implantation therein. The coronary stent is characterized by its ability to be expanded radially to a larger diameter after initial implantation and means for causing said stent to expand to a larger diameter and a method for transporting, positioning and implantation of such coronary stent transluminally to have said stent act as a permanent prosthesis to assure vascular patency. And method for simultaneous angipolasty and stent implant procedure.

10 Claims, 2 Drawing Sheets

INTRACORONARY STENT AND METHOD OF SIMULTANEOUS ANGIOPLASTY AND STENT IMPLANT

FIELD OF THE INVENTION

This invention relates to intravascular implants for maintaining vascular patency in humans and animals. The present invention comprises an open-ended wire formed device of basically cylindrical shape and made of a softer-than spring type metal and fitted over an inflatable element of a typical balloon type catheter such as described in U.S. Pat. No. 4,195,637 and U.S. Pat. No. 4,402,307. The wire formed device is intended to act as a permanent prosthesis stent and is implanted transluminally. Specifically this invention is characterized by the ability of said intravascular stent to be enlarged radially after having been introduced percutaneously, transported transluminally and positioned at a desired location. In addition, this invention relates to a method whereby a permanent prosthesis stent is implanted at the same time the angioplasty procedure is being performed. This invention is particularly useful in transluminal implantation of a stent in the field of cardiology and especially in the case of coronary angioplasty to prevent restenosis.

BACKGROUND OF THE INVENTION

In my U.S. Pat. No. 4,649,922 a device is described in combination with a catheter which is basically a compression spring retained between a partially inflated balloon and an abutment immediately behind the balloon on the catheter shaft. The intent is to transport the spring prosthesis in this manner to the desired location and then after a successful angioplasty procedure release said spring prosthesis by totally evacuating said balloon, thus allowing said spring prosthesis to expand linearly and stay in place while the balloon catheter is withdrawn. This method is quite simple and its simplicity is very attractive; however it has some drawbacks. One and foremost is the fact that the spring has a fixed diameter and as such is unable to fully conform to the inside wall of the vessel which at times is quite tortuous and thus could conceivably create a somewhat turbulant flow of blood, and possible thrombosis could in some cases result. Other Patents, e.g. No. 4,553,545 teach a different method where a relatively complex mechanical rotating device and co-axial cables are employed to achieve the necessary means to change the diameter of the implanted stent to a larger dimension at the point of implant. Still other Patents, e.g. No. 3,868,956 describe a method wherein a temperature responsive metalic device is used and expanded after implant using external heat sources. All of the above mentioned devices present drawbacks of various magnitudes including blood coagulation and possble thrombosis, and considerable complexity of procedure.

In angioplasty procedures at this time, in many cases restenosis occures soon thereafter, which requires a secondary procedure or a surgical bypass operation. The implanted prosthesis as described herein will preclude such additional procedures and will maintain vascular patency indefinately.

Depending on the size used, the device according to this invention can also be efficacious in other, similar applications, such as: repair of aneurisms, support of artificial vessels or liners of vessels, stabilization of interior vessel tubes, e.g. bronchial tubes, retention of embolii and plaque and mechanical support to prevent collapsing of dialated vessels. Still many other and similar applications will be satisfied by this invention without departing from the basic premise and concept.

This device particularely allows a single percutaneous transluminal angioplasty procedure to combine the essential angioplasty itself using any standard balloon-type catheter to recanalize an obstructed vessel with the implantation of a permanent prosthesis stent in one single procedure thereby reducing the risk factor and the trauma by a considerable degree for the patient undergoing such procedure.

Other reference publications:

1. Self-expanding metalic stents for small vessels, Radiology 1987—162.469-472.
2. Intravascular stents to prevent to prevent occlusion and restenosis after transluminal angioplasty. N.E.J. of Med. Mar. 19, 1987. describes experiments with a stent on animals.
3. U.S. Pat. No. 4,580,568 Percutaneous endovascular stent.
4. U.S. Pat. No. 4,503,569 transluminally placed expandable graft prosthesis, Dotter 1985.
5. U.S. Pat. No. 4,699,922 Catheter arrangement having a variable diameter tip and spring prosthesis, Wiktor 1987.

All of the above references describe or teach various methods of providing or otherwise introducing stents or different types for applications similar to one described in this invention.

SUMMARY OF THE INVENTION

The improvement of this invention over other similar devices such as cited in patents above, and specifically my previous invention described in U.S. Pat. No. 4,649,922, is the ability of the device of this invention to allow for and to maintain a very low profile and a small frontal area, so very important for purposes of percutaneous insertion. Thus the stent of this invention can be inserted into and be transported via a standard #8F Guiding Catheter such as USCI Cat. #006128, while using standard procedures and methods. Once on location, the stent can be expanded radially to a diameter larger then initially introduced; a ratio of=2½:1 can easily be achieved with a wire diameter of 0.008 and initial stent diameter of 0.075. The expanded larger diameter will conform to the inside of the vessel and maintain intimate contact with the inside wall. The stent of this invention is characterized by the low memory level of the relatively easily deformable metal used for the wire.

The configuration of the stent 1, shown in FIG. 1, is such that the wire 3 is coiled having a limited number of turns wound in one direction 4 then reversed and wound in the opposite direction 5 with the same number of turns, then reversed again and so on until a desired length L is obtained. In order to create this stent 1 and to assume the configuration as shown in FIG. 1 a length of selected wire is wound on a mandrel of given diameter for 3 turns stpped and reversed forming a tight loop 6 of approximately 3-4 wire diameters. At this point pressure is applied to inside of loop 6 with a pressure finger (not shown) to prevent the wire from unwinding when the direction of winding is reversed.

The purpose of having only a limited number of turns wound in one direction then reversed and having the same number of turns wound in the opposite direction is to allow for radial expansion of stent 1 when controlled pressure, such as applied by an inflated balloon 7, is applied from the inside of said stent 1.

This condition is well illustrated in FIG. 5. The radial expansion is achieved and accomplished by partial uncoiling and unwinding of one or two turns or parts thereof until a larger diameter is obtained. The dimensions of the enlarged diameter is dictated and determined by the diameter to which the balloon is inflated. By comparison, a typical coil spring, in which all of the coils are wound in the same direction, cannot readily be expanded radially regardless of the magnitude of pressure applied to the inside of such coil spring, due to considerable friction between the coils and the surrounded media such as the balloon. The friction of a coil spring around any object increases exponentially with number of turns. Such principle is typically used on a capstan. In my invention, characterized by the construction and configuration of the stent 1, the friction increases linearly with each group of turns, thus radial expansion is easily accomplished in a controlled manner. FIG. 2 shows a typical balloon 7 such as commonly used for angioplasty disposed within stent 1, the balloon 7 being in its deflated condition. The reversing loops 6 of stent 1 are lightly crimped so that they grip the balloon to provide enough friction to prevent stent 1 from sliding and slipping off the balloon 7 during transportation and deployment.

An alternate method to produce the stent is to wind the wire directly over the balloon, in which case the balloon itself becomes the mandrel. In this preferred method, the tightness of the stent over the balloon is better controlled and the assembly is controlled by the manufacturer assuring proper quality. Reversing loops 6 are circumferentially skewed and angularly displaced from one another with respect to the linear axis of the stent so as not to be in line in order to avoid a seam effect, and to provide a better balanced support. At the same time the non-alignment of loops 6 permits more uniform flexing of the stent during deployment, to follow the natural bends within the cardiovascular system, and especially after expansion and implantation to provide even and free flexing with natural body movements.

An object of this invention is the provision of a coiled wire stent which allows easy expansion and subsequent retention of the expanded shape within the vessel.

Still another object of this invention is the simplicity of its application, especially with respect to angioplasty, where one single procedure accomplishes two distinct functions. The stent being initially placed and fitted over the balloon is expanded at the same time and by the action of inflation of the balloon, where the first function is to compress the plaque, thus creating a recanalized lumen as characterized by angioplasty, and the second function is to deploy and anchor a permanent stent prosthesis within the newly created recanalized lumen to prevent reclosure, reatenosis and to maintain a free flow of blood indefinately. Both of those functions are accomplished simultaneously and with a single insertion of the catheter.

DESCRIPTION OF THE PREFERRED EMBODYMENT

For purposes of better and clearer understanding of this invention reference is made to FIGS. 1–6. The preferred embodiment of this invention is shown and described in an application for angioplasty; however, it is understood that other applications not specifically mentioned herein are possible and no limitations in scope of this invention are intended or implied without departing from the basic principles of this invention.

Figure 1:
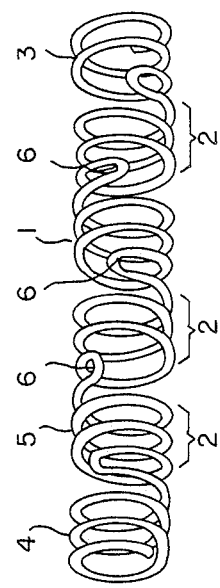
FIG. 1 is a side elevation of a preferred embodiment of a stent according to this invention.

FIG. 1 shows the details of construction of the prosthesis stent 1, hereafter called the stent, which is basically of a hollow cylindrical shape. Stent 1 is basically a tubular shape of coiled wire wound in a special manner comprising a number of groups of turns 2. The wire is made of drawn low memory level material such as copper alloy 110 titanium ASTM F63-83 Grade 1 or gold K 19-22. In the case of copper, the wire is coated with biologically compatible polyester or Teflon. Titanium or gold are biologically inert, therefore those skilled in the art need no further description.

Figure 2:
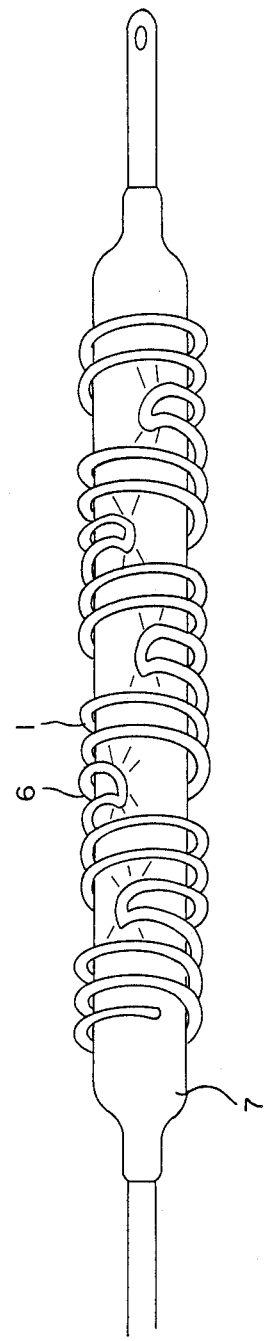
FIG. 2 is a side elevation showing an overall view of a stent prosthesis fitted over a deflated balloon prior to insertion.

In FIG. 2 it is shown, that the stent 1 is centrally located and positioned with respect to length of balloon 7, and that individual coils are evenly spaced so that when expanded, the stent 1 will provide an even support inside the vessel 8 (FIG. 3) and be able to resist external loading.

Figure 3:
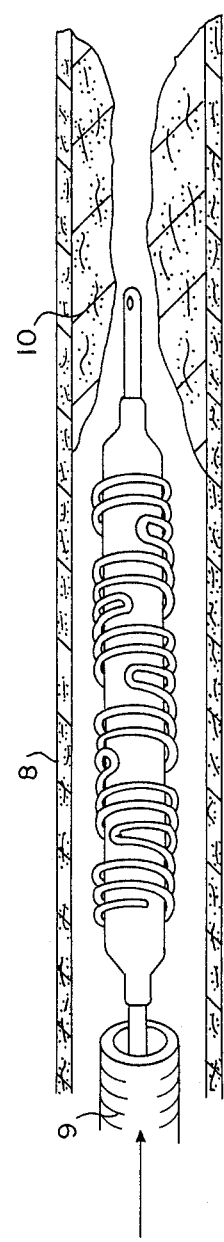
FIG. 3 shows the balloon and stent assembly advanced within a vessel, approaching a partial occlusion.
Figure 4:
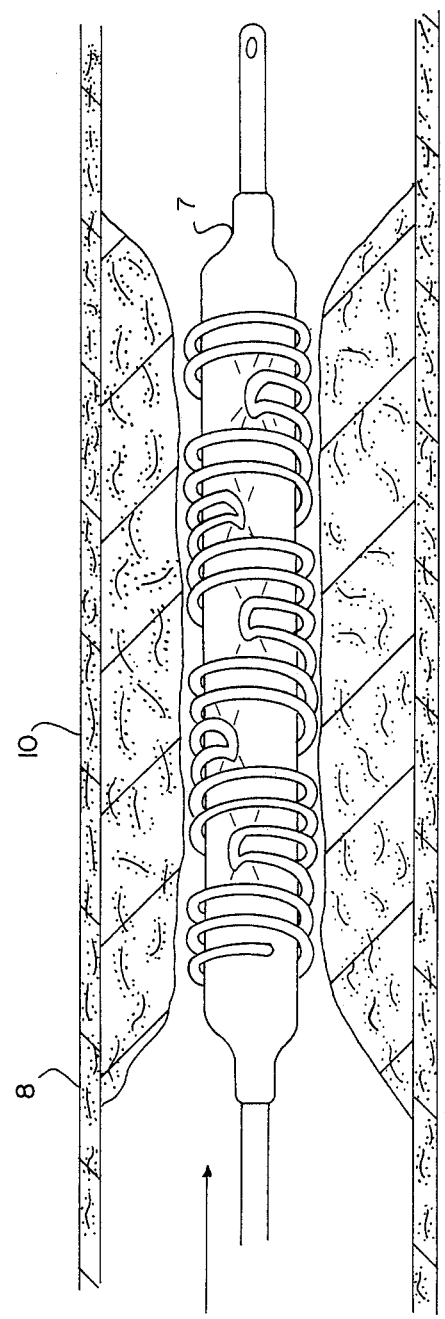
FIG. 4 is similar to FIG. 3 showing the balloon and stent assembly inside a partially obstructed vessel.
Figure 5:
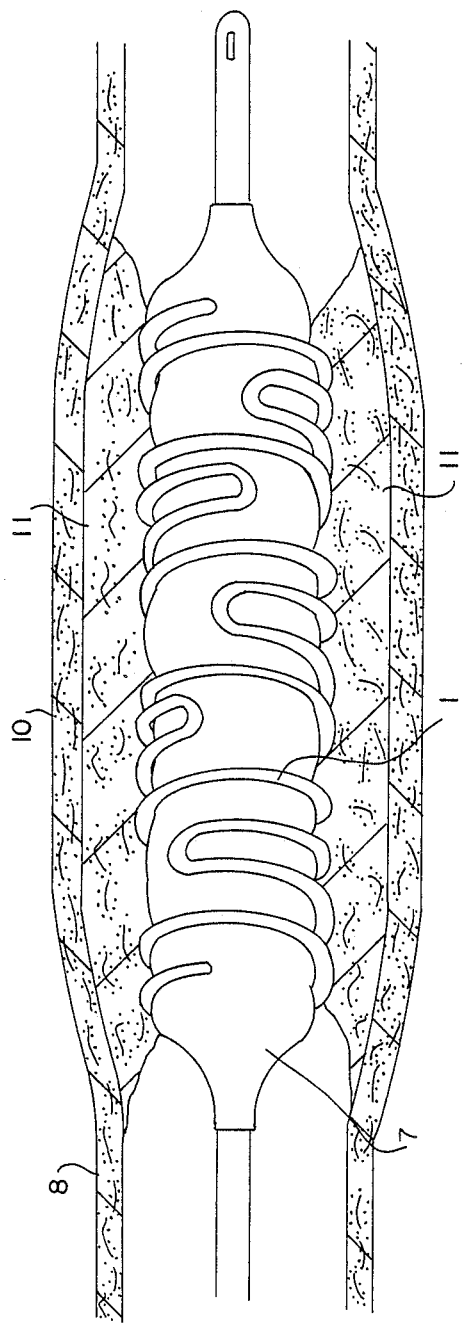
FIG. 5 is similar to FIG. 4, the balloon shown inflated, and the stent radially expanded, illustrating the preferred method of an angioplasty procedure coupled with a simultaneous deployment and implantation of a permanent prosthesis stent.

In FIG. 3 it is shown how the stent 1 fitted over the balloon 7 emanates from from a guiding catheter 9 inside vessel 8 and is advanced toward partial occlusion 10. In FIG. 4 it is shown how balloon 7 and stent 1 are located inside occlusion 10 within artery 8, balloon 7 still being in a deflated and low profile condition. Once positively located inside occlusion 10, balloon 7 is inflated using standard angioplasty procedures and techniques. As balloon 7 expands so does the stent 1, as shown in FIG. 5. The expanding balloon 7 causes plaque 11 to compress, while simultaneously expanding stent 1 follows and supports and contains the plaque 11 preventing the plaque from again reoccluding vessel 8.

Figure 6:
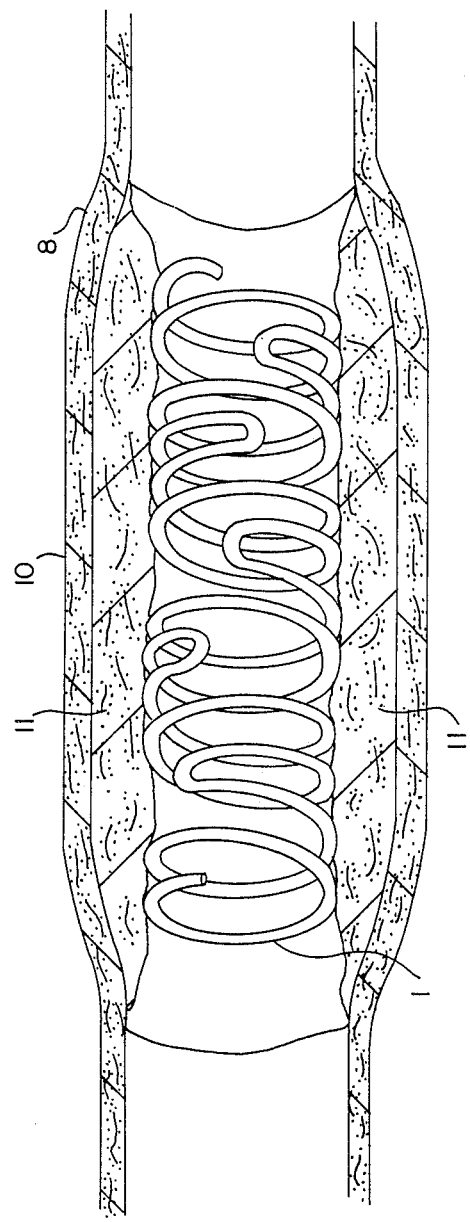
FIG. 6 is a view similar to FIG. 5 showing the prosthesis stent implanted and plaque compressed and retained, after removal of the balloon.

Angioplasty procedure now completed, balloon 7 is deflated and withdrawn leaving stent 1 firmly implanted within vessel 8. The previously occluded part 10 of vessel 8 is now positively recanalized and complete patency restored. FIG. 6 shows stent 1 firmly implanted and imbedded in compressed plaque 11, providing both an adequate support as well as a smooth lumen void of protrusions, a very desireable condition, since any protrusions are conducive to turbulant flow of blood and potential formation of thrombosis.

To test the viability of the principle of this invention, a polyester-coated copper wire approx. 0.009" dia. was wound on a mandrel 0.063" dia. in a manner described earlier with 4 turns wound CW then reversed and 4 turns CCW, and so on. This wire wound form was then removed from the mandrel and placed over a 3.5 mm balloon type LP DILACA, and the balloon subsequently inflated using air and a standard 10 cc disposable syringe. It was observed that liquid, such as plain water, was a better inflating medium then air and so it was used for subsequent tests all with acceptable results. Various sizes of wire and different materials were used to determine optimum combinations. To simulate clinical conditions, and to observe the mode of expansion of the stent inside a vessel, a model stent was made of 0.008" dia. copper wire, and placed over a 3.5 mm balloon, and the assembly was inserted inside a Latex tubing 2.5 mm inside diameter and 0.8 mm wall. The balloon was inflated and expansion of the stent was observed through the translucsent wall of the tubing while it progressed as intended. Deflating the balloon left the stent firmly implanted inside the experimental Latex tubing. Further experiments showed that multiple stents can be used. In fact, a typical balloon as shown in FIG. 2 fitted with a stent can be fed through a previously expanded stent, said second stent being placed ahead of said first stent for multiple implants.

Clinical tests on animals are presently being conducted, and initial results are very encouraging and promising.

While this invention described and illustrated herein depicts a typical application for coronary implant, it is to be understood that the above is considered to be of illustrative and non-restrictive character, since similar procedures and techniques can be applied to several other applications and uses without departing from the basic scope and spirit of this invention.

I claim:

1. A radially expandable stent for implantation within a body vessel, comprising
    a wire winding in a hollow cylindrical shape,
    the winding including a series of groups of helical coils along the length of the winding for providing radial strength,
    the coils of each group being wound in a direction opposite to the direction of winding of the next adjacent group of coils,
    a reversely-turned loop joining each two successive groups of coils for allowing smooth expansion of the adjacent groups of coils, and
    means within the wire winding for expanding the winding.

2. A stent as defined in claim 1 wherein each reversely-turned loop is angularly spaced from every other reversely-turned loop of the stent.

3. A stent as defined in claim 1 wherein the unexpanded stent has an outside diameter less than 0.075 inch.

4. A stent as defined in claim 1 wherein the stent is radially expandable to approximately three times its original diameter.

5. A stent as defined in claim 4 wherein in its expanded condition, each group of coils includes at least one full coil.

6. A stent as defined in claim 1 wherein said expanding means is an expandable balloon extending longitudinally within the winding.

7. A stent as defined in claim 6 wherein at least some of the reversely-turned loops are bent toward the axis of the stent so that they tend to grip the balloon.

8. A method of treating a body vessel, comprising the steps of:
    providing a stent wound wire having a hollow cylindrical shape, the stent being radially expandable and having the ability to retain its shape after expansion,
    providing a balloon within the stent, the balloon being at least partially deflated,
    inserting the stent and balloon into a body vessel having at least a partial occlusion and then along the vessel until they reach the occlusion,
    expanding the balloon so as to expand the stent against the inner surface of the vessel to open the occlusion and simultaneously expand the stent, and
    deflating and removing the balloon while leaving the expanded stent in place.

9. A method as defined in claim 8 including the step of inserting a second stent and a balloon within it through a first expanded stent, and expanding the balloon and second stent at a point longitudinally offset from the first stent.

10. A radial expandable stent for implantation within a body vessel comprising:
    a stent body having a hollow cylindrical shape, the body including multiple helical coils along the length of the body, each coil including at least one complete turn,
    the turns of each coil being wound in a direction opposite to the direction of winding of the adjacent coils, and
    means for connecting the helical coils.

* * * * *